US008605986B2

(12) United States Patent
Tang

(10) Patent No.: US 8,605,986 B2
(45) Date of Patent: Dec. 10, 2013

(54) BURR DETECTING APPARATUS AND BURR DETECTION METHOD THEREOF

(75) Inventor: Pei-Chong Tang, Tu-Cheng (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 219 days.

(21) Appl. No.: 13/031,577

(22) Filed: Feb. 21, 2011

(65) Prior Publication Data

US 2011/0235896 A1 Sep. 29, 2011

(30) Foreign Application Priority Data

Mar. 26, 2010 (CN) .......................... 2010 1 0133482

(51) Int. Cl.
*G06K 9/00* (2006.01)

(52) U.S. Cl.
USPC ........... 382/147; 382/144; 382/146; 382/149; 382/150

(58) Field of Classification Search
USPC .................. 382/141, 144, 145, 147, 149, 150
See application file for complete search history.

(56) References Cited

U.S. PATENT DOCUMENTS 5,485,532 A * 1/1996 Ishihara ........................ 382/205
5,586,199 A * 12/1996 Kanda et al. ................. 382/197

* cited by examiner

*Primary Examiner* — Brian Q Le
*Assistant Examiner* — Michael Vanchy, Jr.
(74) *Attorney, Agent, or Firm* — Altis Law Group, Inc.

(57) ABSTRACT

A burr detection apparatus includes an imaging unit and a detection unit. The imaging unit captures an original image of a stencil. The original comprises black and white pixels. The detection includes a CPU and a memory. The CPU includes an extracting module, a deciding module, a counting module, and a comparing module. The extracting module obtains a matrix image with N*N pixels, wherein N is an odd number. The deciding module decides whether the center pixel of the matrix image is a black pixel. The counting module obtains a black pixel total counted among marginal pixels which position in the margin of the matrix image in a predetermined rule. The comparing module compares the black pixel total with a predetermined threshold number, and determines that the part of the stencil corresponding to the matrix image has a burr when the black pixel total is less than the threshold number.

10 Claims, 8 Drawing Sheets

Start
Captures an original image of a stencil — S602
Obtains a number of matrix images from the original image — S604
Determines if the center pixel is a black pixel — S606 (No / Yes)
Counts the black pixels amoung the marginal pixels in a predetermined rule to obtain a value — S608
Determines whether the value is less than a pretermined threshold number — S610 (No / Yes)
Send a burr detection result of the matrix image to the display unit — S612
End

BURR DETECTING APPARATUS AND BURR DETECTION METHOD THEREOF

BACKGROUND

1. Technical Field

The present disclosure relates to a burr detection apparatus and a burr detection method thereof.

2. Description of Related Art

Surface mounting technology machines utilize a stencil, which defines holes or slots to paste solder onto a printed circuit board. The stencil always includes burrs retained within the holes and slots, causing an improper adhesion between the solder onto the printed circuit board. Thus, the burrs of the stencil should be detected and then removed. In conventional testing technology, the burrs are mainly detected manually by naked eye, which is of very low efficiency and time consuming.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Embodiments of the present disclosure will now be described in detail below, with reference to the accompanying drawings.

Figure 1:
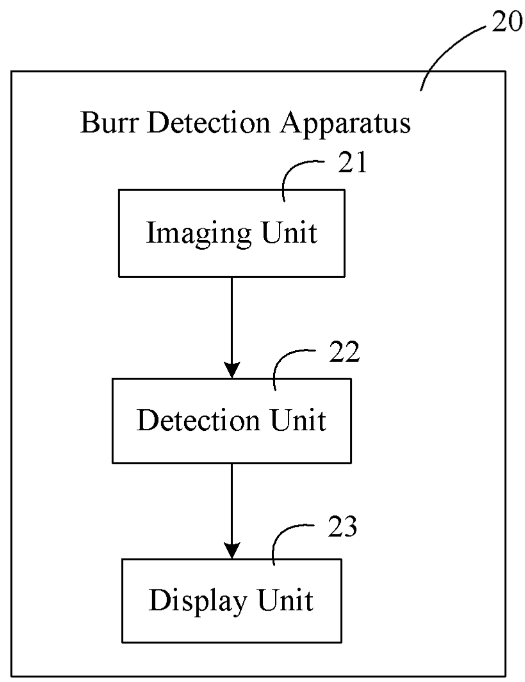
FIG. 1 is a block diagram view of a burr detection apparatus according to an exemplary embodiment.

Referring to FIG. 1, a block diagram view of a burr detection apparatus 20 according to an exemplary embodiment is illustrated. The burr detection apparatus 20 includes an imaging unit 21, a detection unit 22, and a display unit 23.

Figure 2:
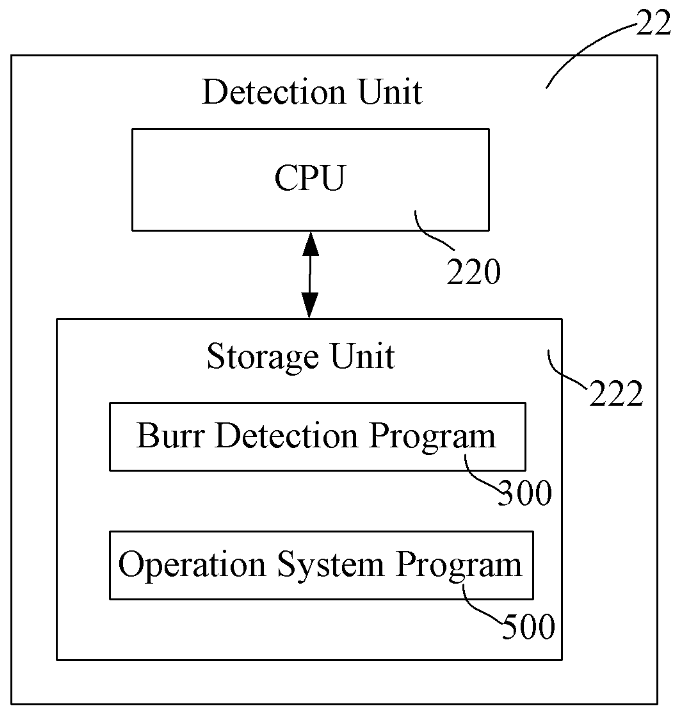
FIG. 2 is a block diagram view of a detection unit of the detection apparatus of FIG. 1.

Referring also to FIG. 2, the imaging unit 21 is configured to capture an original image 100 of a stencil. The original image 100 includes a number of black pixels and white pixels.

Figure 3:
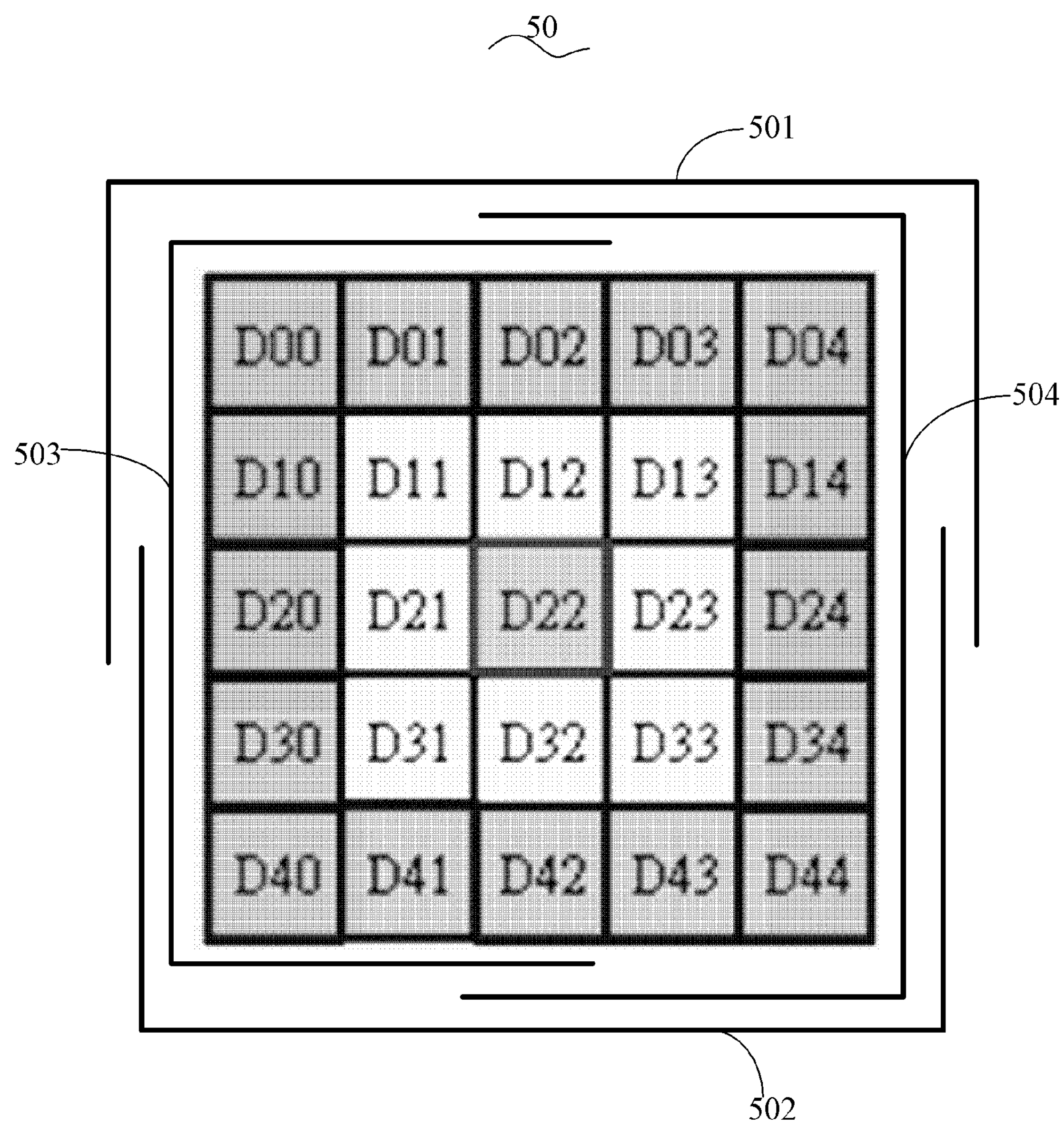
FIG. 3 is a schematic view of a matrix image.

Referring to FIG. 3, the detection unit 22 includes a CPU 220 and a memory 221. The CPU 220 includes an extracting module 222, a deciding module 223, a counting module 224, a comparator module 225, and an output module 226.

Figure 4:
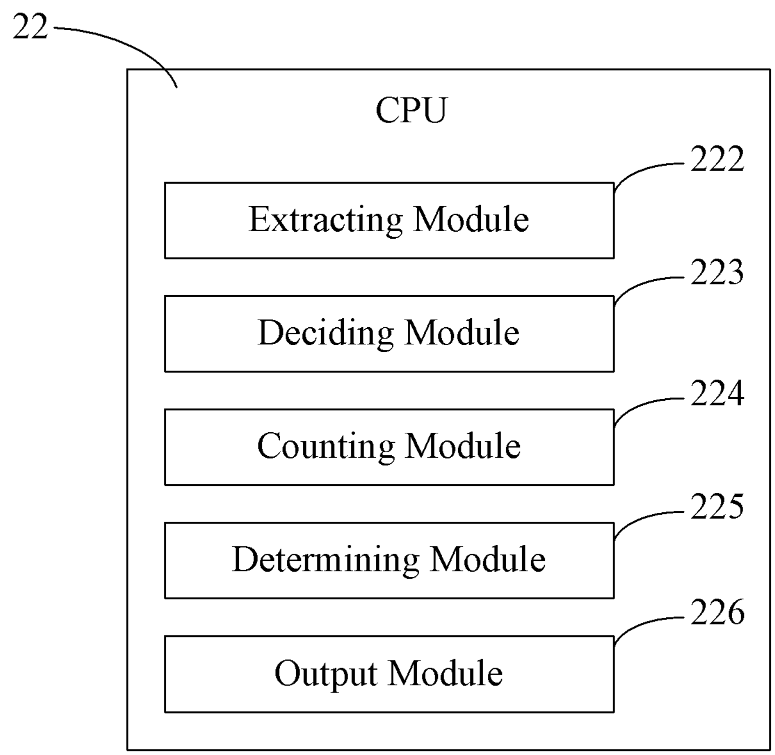
FIG. 4 is a block diagram view of a CPU of the detection unit of FIG. 3.

Referring to FIG. 4, the extracting module 222 is configured to obtain a matrix image 50 with N*N pixels from the original image 100, wherein N is an odd number, such as 3, 5, and 7. For better understanding the present disclosure, the pixel positioned in the center of the matrix image 50 is regarded as a center pixel and the pixels positioned in the margin of the matrix image 50 are regarded as marginal pixels. The marginal pixels positioned on the top margin of the matrix image 50 are regarded as top marginal pixels 501.

The marginal pixels positioned on the bottom margin of the matrix image 50 are regarded as bottom marginal pixels 502. The marginal pixels positioned on the left margin of the matrix image 50 are regarded as left marginal pixels 503, and the marginal pixels positioned on the right margin of the matrix image 50 are regarded as right marginal pixels 504. For example, D22 is regarded as the center pixel, and D00, D01, D02, D03, D04, D10, D14, D20, D24, D30, D34, D40, D41, D42, D43, and D44 are regarded as the marginal pixels. D00, D01, D02, D03, D04, D10, and D14 are regarded as top marginal pixels. D20, D24, D30, D34, D40, D41, D42, D43, and D44 are regarded as bottom marginal pixels. D00, D01, D02, D10, D20, D30, D40, D41, and D42 are regarded as left marginal pixels. D02, D03, D04, D14, D24, D34, D44, D43, and D42 are regarded as right marginal pixels.

Figure 5:
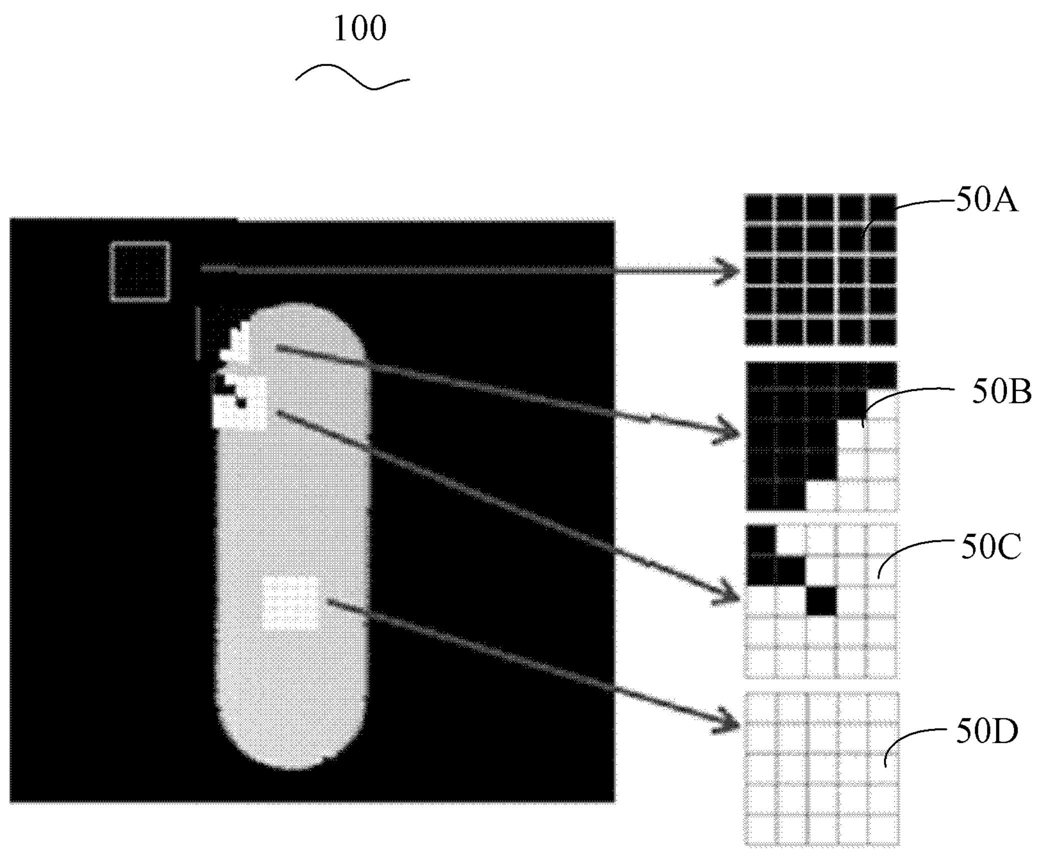
FIG. 5 is a schematic view of an original image.
Figure 6:
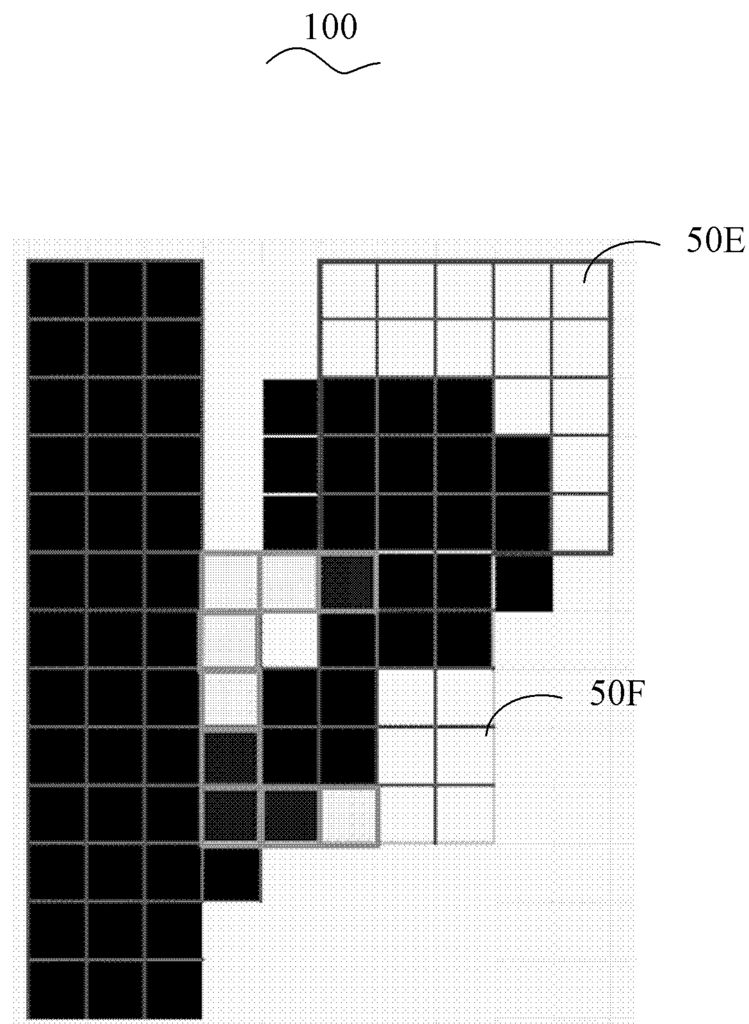
FIG. 6 is a schematic view of another original image.

The deciding module 223 is configured to decide whether the center pixel of the matrix image 50 is a black pixel. As shown in FIGS. 5 and 6, the center pixels of the matrix images 50A, 50B, 50C, 50E, and 50F are black pixels, and the center pixel of the matrix image 50D is a white pixel.

The counting module 224 is configured to count the marginal pixels of the matrix image 50 in a predetermined rule to obtain a quantity.

The comparing module 225 is configured to compare the black pixel total with a predetermined threshold number. Because most of the burrs have a sharp head corresponding to the center pixel and a flat rear corresponding to the marginal pixels. If the quantity is less than the threshold number, the comparing module 225 determines that the part of the stencil corresponding to the matrix image 50 has a burr.

In a first predetermined rule, the quantity obtained by the counting module 224 is a total of black pixels among all the marginal pixels of the matrix image 50. As shown in FIG. 5, the quantity of the matrix images 50A, 50B, and 50C are respectively 16, 10, and 2. Assuming the threshold number is 5, the part of the stencil corresponding to the matrix image 50C is determined to have a burr.

In a second predetermined rule, the quantity obtained by the counting module 224 is the maximum total of black pixels among the top marginal pixels, the bottom marginal pixels, the left marginal pixels, and the right marginal pixels. That is, the counting module 224 respectively counts the black pixels among the top marginal pixels, the bottom marginal pixels, the left marginal pixels, and the right marginal pixels, obtains four totals of black pixels, and regards the maximum total among four totals as the quantity of the matrix image 50. For example, as shown in FIG. 6, the totals of the top marginal pixels, the bottom marginal pixels, the left marginal pixels, and the right marginal pixels of the matrix image 50E are respectively 1, 6, 5 and 2. The totals of the black pixels of the top marginal pixels, the bottom marginal pixels, left marginal pixels, and the right marginal pixels of the matrix image 50F are respectively 4, 3, 4, and 4. Thus, the quantity of the matrix images 50E and 50F are respectively 6 and 4. Assuming the threshold number is 7, the part of the stencil corresponding to the matrix images 50E and 50F are determined to have a burr.

The output module 226 is configured to output a message to the display unit 23. For example, in the embodiment, the output module 226 outputs a burr detection result generated from the comparing module 225 to the display unit 23.

Referring to FIG. 6, in another embodiment, the detection unit 22 includes a memory 221 and a field-programmable gate array integrated circuit 400 (hereinafter "FPGA integrated circuit"). The memory 221 is configured to store a number of matrix images 50 from the original image 100 of the stencil. The FPGA integrated circuit 400 is configured to determine whether a part of the stencil corresponding to each of the matrix images 50 has a burr. The FPGA integrated circuit 400 includes an addressing circuit 401, a reading circuit 402, a data conversion circuit 403, an arithmetic circuit 404, a comparator circuit 405, and an output circuit 406.

The addressing circuit 401 is configured to provide coordinates information of the matrix images 50 on the original image 100 to the data conversion circuit 402.

The data conversion circuit 402 is configured to code each pixel of the matrix images 50 in the memory 222. For example, the data conversion circuit 402 codes the black pixel as "1" and the white pixel as "0".

The reading circuit 403 is configured to read the codes of the center pixel and the marginal pixels of the matrix images 50.

The deciding circuit 404 is configured to detect whether the code of the center pixel is "1". If yes, the deciding circuit 404 determines that the center pixel is a black pixel, and the arithmetic circuit 405 obtains a quantity by summing up the codes of the marginal pixels in a predetermined rule.

The comparator circuit 406 is configured to compare the quantity with a threshold number. If the quantity is less than the threshold number, the part of the stencil corresponding to the matrix image 50 is determined to have a burr.

The output circuit 406 is configured to output a burr detection result of the matrix image 50 to the display unit 23.

Figure 7:
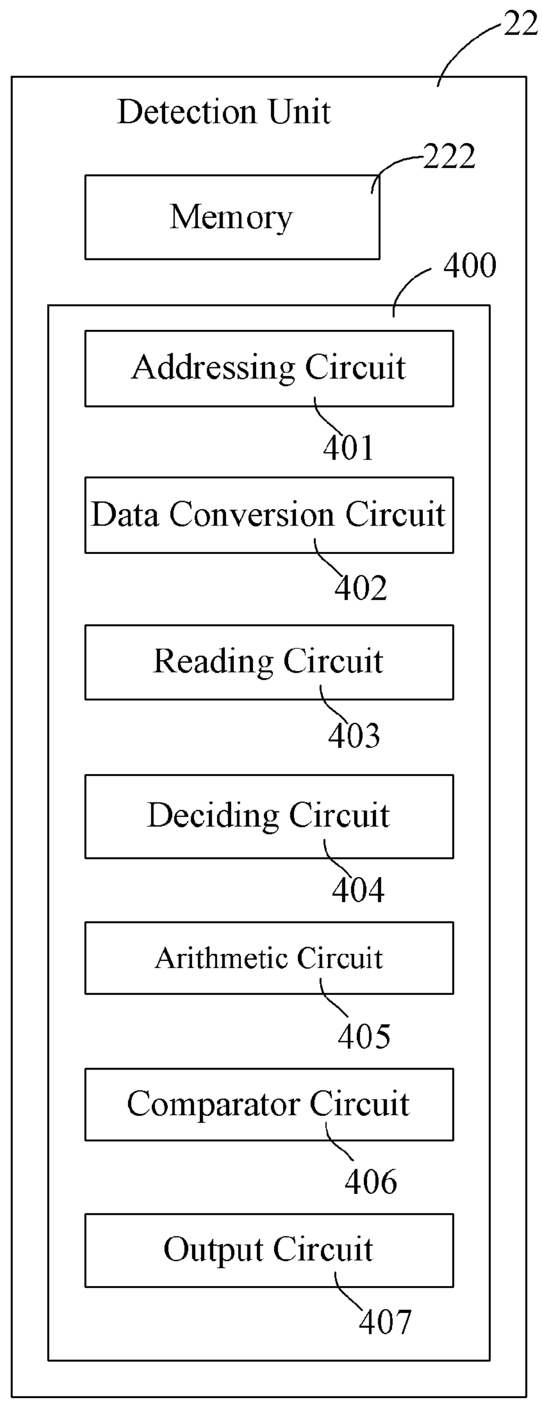
FIG. 7 is a block diagram view of a detection unit according to another embodiment.
Figure 8:
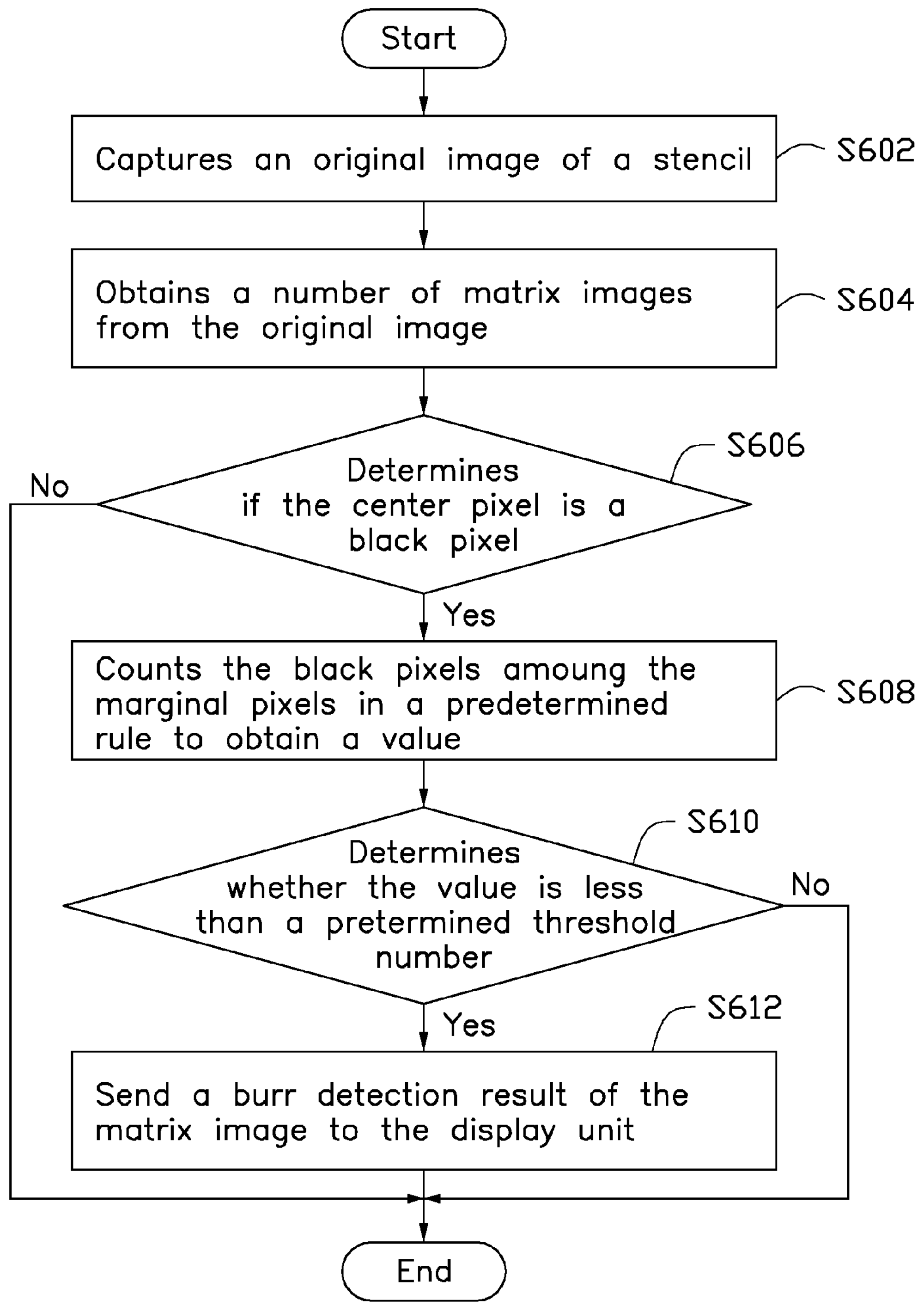
FIG. 8 is a flowchart view of a burr detection method according to an exemplary embodiment.

Referring to FIG. 7, a flow chart of a burr detection method implemented by the burr detection apparatus 20 according to an exemplary embodiment is illustrated.

In step 602, the imaging unit 21 captures an original image 100 of a stencil. The original image 100 includes a number of black pixels and white pixels.

In step 604, the extracting module 222 obtains a number of matrix images 50 from the original image 100. The matrix image 50 includes a center pixel and a number of marginal pixels.

In step 606, the deciding module 223 decides if the center pixel of the matrix image 50 is a black pixel.

If yes, in step 608, the counting module 224 obtains a black pixel total counted among the marginal pixels of the matrix image 50 in a predetermined rule.

In step 610, the comparator module 225 compares the black pixel total of the matrix image with a predetermined threshold number. If the black-pixel number is less than the threshold number, a part of the stencil corresponding to the matrix image is determined to have a burr.

The output module 226 sends a burr detection result of the matrix image 50 to the display unit 23 to display thereon.

While various embodiments have been described and illustrated, the disclosure is not to be constructed as being limited thereto. Various modifications can be made to the embodiments by those skilled in the art without departing from the true spirit and scope of the disclosure as defined by the appended claims.

What is claimed is:

1. A burr detection apparatus comprising:

an imaging unit configured to capture an original image of a stencil, wherein the original image comprises a plurality of black pixels and white pixels; and a detection unit comprising a CPU and a memory, wherein the CPU comprises:

an extracting module configured to obtain a matrix image with N*N pixels from the original image, wherein N is an odd number;

a deciding module configured to determine whether a center pixel of the matrix image is a black pixel;

a counting module configured to count black pixels positioned in the margin of the matrix image in a predetermined rule to obtain a quantity when the deciding module determines that the center pixel of the matrix image is a black pixel; and a comparing module configured to compare the quantity with a predetermined threshold number, and determine that the part of the stencil corresponding to the matrix image has a burr when the quantity is less than the threshold number.

2. The burr detection apparatus as described in claim 1, further comprising a display unit, wherein the CPU further comprises an output module to send a burr detection result to the display unit.

3. The burr detection apparatus as described in claim 1, wherein in the predetermined rule, the quantity obtained by the counting module is a total of black pixels among all the marginal pixels of the matrix image.

4. The burr detection apparatus as described in claim 1, wherein in the predetermined rule, the quantity obtained by the counting module is the maximum among the totals of the black pixels of the top marginal pixels, the bottom marginal pixels, the left marginal pixels, and the right marginal pixels of the matrix image.

5. A burr detection apparatus comprising: an imaging unit configured to capture an original image of a stencil, the original image comprises a plurality of black pixels and white pixels; and a detection unit comprising:

a memory configured to store a number of matrix images from the original image of a stencil; and a FPGA integrated circuit comprising:

an addressing circuit configured to provide coordinates information of the matrix images on the original image;

a data conversion circuit configured to code each black or white pixel of the matrix images in the memory;

a reading circuit configured to read the codes of a center pixel and the marginal pixels of the matrix images;

a deciding circuit configured to detect whether the center pixel is a black pixel;

an arithmetic circuit configured to count black pixels positioned in the margin of the matrix image in a predetermined rule to obtain a quantity when the deciding module determines that the center pixel of the matrix image is a black pixel; and a comparator circuit configured to compare the black pixel total with a predetermined threshold number when the center pixel is a black pixel, wherein when the black pixel total is less than the predetermined threshold, the part of the stencil corresponding to the matrix image is determined to have a burr.

6. The burr detection apparatus as described in claim 5, wherein the burr detection apparatus further comprises a display unit, the FPGA integrated circuit further comprises an output circuit to send a burr detection result to the display unit.

7. The burr detection apparatus as described in claim 5, wherein in the predetermined rule, the quantity obtained by the counting module is a total of black pixels-among all the marginal pixels of the matrix image.

8. The burr detection apparatus as described in claim 5, wherein in the predetermined rule, the quantity obtained by the counting module is the maximum among the totals of the black pixels of the top marginal pixels, the bottom marginal pixels, the left marginal pixels, and the right marginal pixels of the matrix image.

9. A burr detection method applied to a burr detection device, the burr detection device comprising an imaging unit and a CPU, the method comprising:

controlling the imaging unit to capture an original image of a stencil via the CPU;

obtaining a number of matrix images with N*N pixels from the original image via the CPU, wherein N is an odd number;

deciding if a center pixel of the matrix image is a black pixel via the CPU;

if yes, counting black pixels positioned in the margin of the matrix image in a predetermined rule to obtain a quantity via the CPU; and comparing the quantity with a predetermined threshold number via the CPU, and if the quantity is less than the threshold number, a part of the stencil corresponding to the matrix image is determined to have a burr.

10. The burr detection method as described in claim 9, further comprising a step sending a burr detection result of the matrix image to the display unit.

* * * * *